Figure 1:
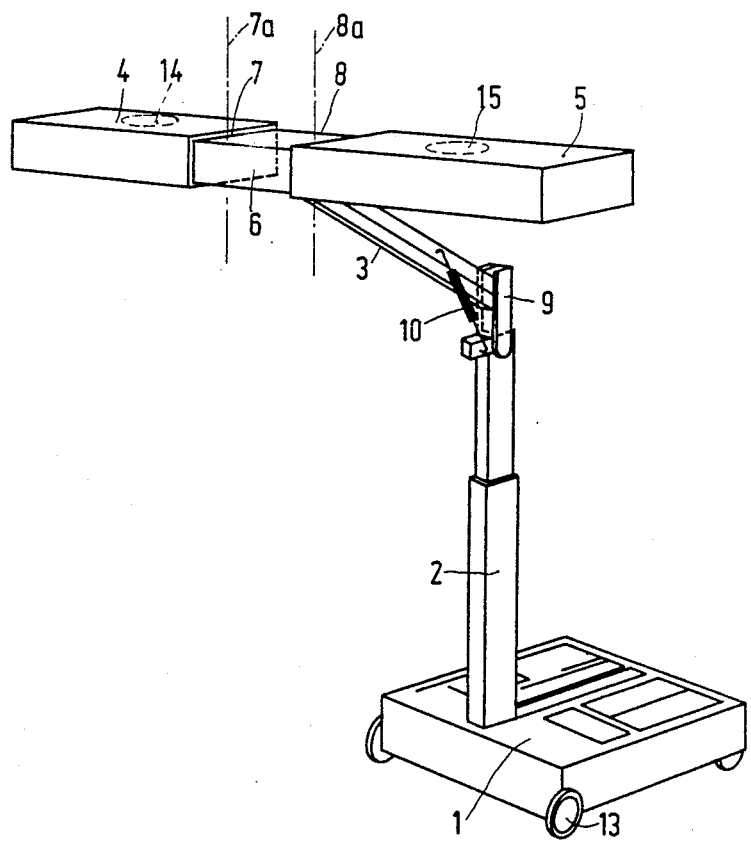

United States Patent [19]

Frankena

[11] Patent Number: 4,950,903
[45] Date of Patent: Aug. 21, 1990

[54] IRRADIATION DEVICE

[76] Inventor: Johannes A. Frankena, Oliemolenstraat 5, Drachten, Netherlands

[21] Appl. No.: 307,660

[22] Filed: Feb. 6, 1989

[30] Foreign Application Priority Data

Feb. 9, 1988 [NL] Netherlands .......................... 8800300

[51] Int. Cl.$^5$ .............................................. A61N 5/06
[52] U.S. Cl. ................................... 250/504 R; 128/396
[58] Field of Search ...................... 250/504 R; 128/396

[56] References Cited

U.S. PATENT DOCUMENTS 4,095,113  6/1978  Wolff .................................... 250/504

FOREIGN PATENT DOCUMENTS

WO85/00527  2/1985  World Int. Prop. O. .......... 128/396

*Primary Examiner*—Jack I. Berman

[57] ABSTRACT

Irradiation device for emitting ultraviolet radiation, comprising a housing accommodating at least one reflector and having a sheet material reflecting wall of substantially parabolic cross-sectional shape both ends of which are provided with reflecting side walls extending slightly obliquely towards the reflector opening, said side plates comprising holders between which a tubular discharge vessel of a high-pressure discharge lamp can be incorporated whose longitudinal axis extends parallel to the longitudinal axis of the parabolic reflecting wall, an elongate shielding plate extending beyond the location where the ends of the discharge vessel are incorporated in the holders being arranged between the discharge vessel and the reflecting wall.

2 Claims, 2 Drawing Sheets

IRRADIATION DEVICE

The invention relates to an irradiation device for emitting ultraviolet radiation, comprising a housing accommodating at least one reflector and having a sheet material reflecting wall of substantially parabolic cross-sectional shape both ends of which are provided with reflecting side walls extending slightly obliquely towards the reflector opening, said side plates comprising holders between which a tubular discharge vessel of a high-pressure discharge lamp can be incorporated whose longitudinal axis extends parallel to the longitudinal axis of the parabolic reflecting wall.

An irradiation device of this type is known from Netherlands patent application No. 8700348 laid open to public inspection and is used for irradiating the human body with ultraviolet radiation. The housing accommodating a plurality of reflectors with radiation sources is pivotably connected to a wheeled base via a telescopic arm. The housing also accommodates a ventilator, mainly for cooling a person lying under the device and for cooling the area directly surrounding the housing.

The tubular discharge vessel of the lamp is secured in holders in the side walls. Special openings are required for this purpose. It has been found that cool air of the ventilator accommodated in the housing is then blown via these openings along the outer surface of the discharge vessel This is a drawback because the temperature of the lamp then decreases below its optimum operating temperature. The efficiency and the radiation output of the lamp thus also decrease.

It is an object of the invention to provide an irradiation device of the type described in the opening paragraph having such a construction that this drawback is obviated to an optimum extent.

According to the invention an irradiation device of this type is therefore characterized in that an elongate shielding plate extending beyond the location where the ends of the discharge vessel are incorporated in the holders is arranged between the discharge vessel and the reflecting wall.

Due to the presence of the said shielding plate cool air is prevented from passing through the opening between the holders and the reflecting side walls and flowing along the surface of the discharge vessel. The lamp then maintains its optimum operating temperature, thus ensuring a maximum possible radiation output. The shielding plate preferably consists of aluminium. It is secured to the wall of the parabolic reflector part located behind the discharge vessel.

At the area of the holders the shielding plate is slightly bent in the direction of the reflector opening, the holders and the juxtaposed openings being shielded. The cool air can then hardly reach the discharge vessel.

In a preferred embodiment of the device according to the invention the shielding plate proximate to the holders has a recess accommodating the end of the discharge vessel of the lamp. Such a shape of the shielding plate has the advantage that it can be provided in a simple manner during the manufacturing process.

Figure 2:
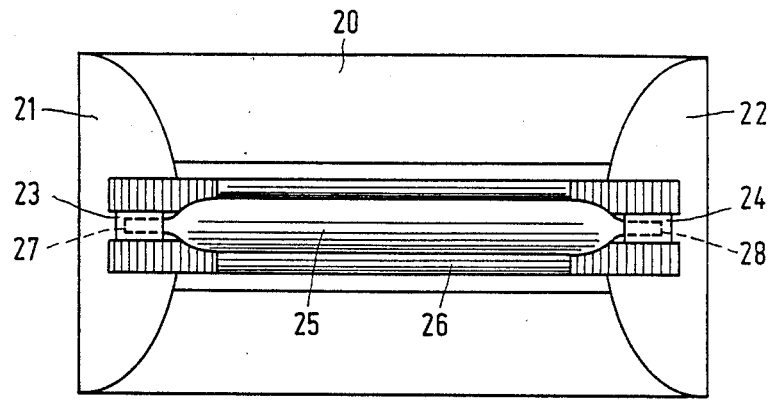
Figure 3:
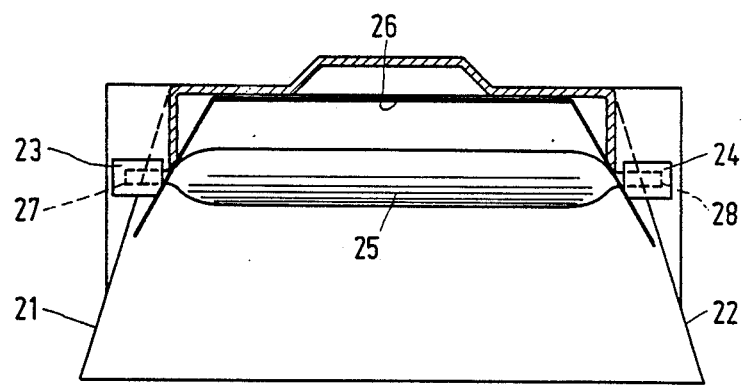

The invention will now be described in greater detail, by way of example, with reference to the accompanying drawings in which FIG. 1 is an elevational view of an irradiation device according to the invention;

FIG. 2 is also an elevational view of a reflector in the housing of the above-mentioned device and FIG. 3 is a longitudinal section of the reflector of FIG. 2.

The irradiation device of FIG. 1 has a base 1 provided with wheels 13, which base is connected to a housing via pivots by means of a telescopic arm 2 and an intermediate arm 3 connected thereto. This housing consists of two elongated parts 4 and 5 which are juxtaposed in a folded state. These parts 4 and 5 accommodate radiation sources (such as high-pressure mercury vapour discharge lamps in which also cobalt and iron are present in the discharge vessel) with reflectors arranged behind them. There are provided two radiation sources per part. A radiation exit side is formed on the side of the two parts facing the base. If the two parts 4 and 5 are placed side by side, the entire system can be collapsed to a compact unit. The said parts 4 and 5 are pivotable with respect to each other about an axis perpendicular to the plane through the radiation exit side (the "horizontal" plane). This is realized by providing the end of the intermediate arm 3 with a coupling member 6 to which the parts 4 and 5 are secured by means of pivots 7 and 8. The longitudinal axes 7a, 8a of these pivots are perpendicular to the plane through the radiation exit side of the parts 4 and 5. The other end of the intermediate arm 3 is pivotably connected to a short pivotal bar 9 secured to the top of the telescopic arm 2. This metal short pivotal bar is bridged by a gas spring 10 whose ends are also pivotably connected to the telescopic arm 2 and the intermediate arm 3, respectively.

A ventilator blowing cool air in the direction of a person to be irradiated is arranged at the location of the centre of each of the parts 4 and 5 (denoted by 14 and 15, respectively). The ventilator is secured to the upper side of 4 and 5' respectively. The cool air leaves the parts 4 and 5 on the lower side. However, due to the presence of a shielding plate in the reflector this air does not influence the temperature of the lamp. This is shown in greater detail in FIG 2.

The reflector consists of a parabolic slightly faceted body 20 of anodized aluminium. This part 20 is mainly parabolic in cross-section. Two reflecting side walls 21 and 22 extending slightly obliquely in the direction of an observer are provided on the ends. These side walls have openings for holders 23 and 24 (see FIG. 3) for a tubular discharge vessel 25 of a high-pressure discharge lamp. The longitudinal axis of the discharge vessel 25 extends parallel to the longitudinal axis of the parabolic part 20. An elongate aluminium shielding plate 26 extending beyond the location where the ends 27 and 28 of the discharge vessel are secured in the holders 23 and 24 is secured between the wall of this part and the discharge vessel. The ends of the shielding plate are slightly bent so as to cover the holes between the holders and the side walls. At that location the shielding plate has recesses. These recesses accommodate the constricted parts of the discharge vessel.

The lamp is a high-pressure metal halide discharge lamp (Philips HPA) having a power of 400 W. The filling of the lamp also comprises some iron and cobalt. The spectrum of the radiation emitted by the lamp not only comprises infrared radiation but mainly UV-A and UV-B radiation as well as some visible light.

What is claimed is:

1. An irradiation device for emitting ultraviolet radiation, comprising a housing accommodating at least one reflector and having a sheet material reflecting wall of substantially parabolic cross-sectional shape both ends of which are provided with reflecting side walls extending slightly obliquely towards the reflector opening said side plates comprising holders between which a tubular discharge vessel of a high-pressure discharge lamp can be incorporated whose longitudinal axis extends parallel to the longitudinal axis of the parabolic reflecting wall, characterized in that an elongate shielding plate extending beyond the location where the ends of the discharge vessel are incorporated in the holders is arranged between the discharge vessel and the reflecting wall.

2. An irradiation device as claimed in claim 1, characterized in that the shielding plate proximate to the holders has a recess accommodating the end of the discharge vessel of the lamp.

* * * * *